(12) United States Patent
Tsuruta

(10) Patent No.: US 10,292,639 B2
(45) Date of Patent: May 21, 2019

(54) INFORMATION PROCESSING DEVICE AND INFORMATION PROCESSING METHOD

(71) Applicant: SONY CORPORATION, Tokyo (JP)

(72) Inventor: Yasushi Tsuruta, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/552,577

(22) PCT Filed: Dec. 16, 2015

(86) PCT No.: PCT/JP2015/085185
§ 371 (c)(1),
(2) Date: Aug. 22, 2017

(87) PCT Pub. No.: WO2016/157641
PCT Pub. Date: Oct. 6, 2016

(65) Prior Publication Data
US 2018/0020971 A1    Jan. 25, 2018

(30) Foreign Application Priority Data

Mar. 27, 2015  (JP) .................................. 2015-066900

(51) Int. Cl.
| | | |
|---|---|---|
| G08B 13/24 | (2006.01) | |
| A61B 5/00 | (2006.01) | |
| A61M 21/00 | (2006.01) | |
| A61B 5/16 | (2006.01) | |
| G06K 9/62 | (2006.01) | |
| G16H 50/00 | (2018.01) | |
| A61B 5/0205 | (2006.01) | |

(52) U.S. Cl.
CPC ............ *A61B 5/4812* (2013.01); *A61B 5/165* (2013.01); *A61B 5/486* (2013.01); *A61B 5/4815* (2013.01); *A61M 21/00* (2013.01); *G06K 9/6262* (2013.01); *G16H 50/00* (2018.01); *A61B 5/0205* (2013.01)

(58) Field of Classification Search
None
See application file for complete search history.

(56) References Cited

U.S. PATENT DOCUMENTS 8,647,253 B2 *  2/2014 Iizuka ................... A61B 3/113
                                                          600/26
9,314,583 B2 *  4/2016 Gavish .................. A61M 21/02
(Continued)

FOREIGN PATENT DOCUMENTS

| JP | 2001-174578 A | 6/2001 |
| JP | 2006-043304 A | 2/2006 |

(Continued)

*Primary Examiner* — Julie B Lieu
(74) *Attorney, Agent, or Firm* — Chip Law Group

(57) ABSTRACT

There is provided an information processing device including: a sleep environment controlling unit configured to, when exerting control of, on the basis of a result of forecast of a transition of a depth of sleep of a user at least in a period from a first time to a second time, a sleeping environment of the user such that the depth of sleep at the second time falls below a first depth-of-sleep threshold value estimated as an upper limit of a first depth-of-sleep region in which the user is likely to awake, decide a temporal pattern of the control in the period from the first time to the second time in accordance with a temporal pattern of the transition.

18 Claims, 11 Drawing Sheets

(56) References Cited

U.S. PATENT DOCUMENTS

| | | | |
|---|---|---|---|
| 2008/0157956 A1* | 7/2008 | Radivojevic | A61B 5/11 340/531 |
| 2009/0192556 A1* | 7/2009 | Wu | A61B 5/0031 607/3 |
| 2011/0021866 A1* | 1/2011 | Iizuka | A61B 3/113 600/26 |
| 2012/0179061 A1* | 7/2012 | Ramanan | A61M 16/024 600/538 |
| 2015/0367097 A1* | 12/2015 | Gavish | A61M 21/02 600/27 |
| 2017/0274174 A1* | 9/2017 | Purdon | A61B 5/0205 |

FOREIGN PATENT DOCUMENTS

| | | |
|---|---|---|
| JP | 2006-43304 A | 2/2006 |
| JP | 2012-110536 A | 6/2012 |

* cited by examiner

INFORMATION PROCESSING DEVICE AND INFORMATION PROCESSING METHOD

CROSS REFERENCE TO RELATED APPLICATIONS

This application is a U.S. National Phase of International Patent Application No. PCT/JP2015/085185 filed on Dec. 16, 2015, which claims priority benefit of Japanese Patent Application No. JP 2015-066900 filed in the Japan Patent Office on Mar. 27, 2015. Each of the above-referenced applications is hereby incorporated herein by reference in its entirety.

TECHNICAL FIELD

The present disclosure relates to an information processing device, an information processing method, and a program.

BACKGROUND ART

Patent Literature 1 describes a technology for assisting a user in rising in accordance with a sleep state of the user by utilizing brain waves. As described in the Patent Literature 1 as well, it is possible to estimate the state of sleep of the user by various biological indicators, such as body motions or pulse, not limited to brain waves, and various technologies for providing services, such as assisting the user in rising by utilizing the result of such estimation have been proposed.

CITATION LIST

Patent Literature

Patent Literature 1: JP2012-110536A

DISCLOSURE OF INVENTION

Technical Problem

It is also conceivable to control the sleeping environment of a user by utilizing a technology as described above such that the user easily awakes at the rising time. However, it is difficult to say that sufficient proposals have been made so far as to which timing such sleeping environment control is executed appropriately, for example. Therefore, the present disclosure proposes an information processing device, an information processing method, and a program being novel and improved that enable sleeping environment control for allowing a user to easily awake at a predetermined time to be executed at appropriate timing.

Solution to Problem

According to the present disclosure, there is provided an information processing device including: a sleep environment controlling unit configured to, when exerting control of, on the basis of a result of forecast of a transition of a depth of sleep of a user at least in a period from a first time to a second time, a sleeping environment of the user such that the depth of sleep at the second time falls below a first depth-of-sleep threshold value estimated as an upper limit of a first depth-of-sleep region in which the user is likely to awake, decide a temporal pattern of the control in the period from the first time to the second time in accordance with a temporal pattern of the transition.

Further, according to the present disclosure, there is provided an information processing method including: when exerting control of, on the basis of a result of forecast of a transition of a depth of sleep of a user at least in a period from a first time to a second time, a sleeping environment of the user such that the depth of sleep at the second time falls below a first depth-of-sleep threshold value estimated as an upper limit of a first depth-of-sleep region in which the user is likely to awake, causing a processor to decide a temporal pattern of the control in the period from the first time to the second time in accordance with a temporal pattern of the transition.

Further, according to the present disclosure, there is provided a program for causing a computer to achieve a function of, when exerting control of, on the basis of a result of forecast of a transition of a depth of sleep of a user at least in a period from a first time to a second time, a sleeping environment of the user such that the depth of sleep at the second time falls below a first depth-of-sleep threshold value estimated as an upper limit of a first depth-of-sleep region in which the user is likely to awake, deciding a temporal pattern of the control in the period from the first time to the second time in accordance with a temporal pattern of the transition.

Advantageous Effects of Invention

According to the present disclosure as described above, sleeping environment control for allowing a user to easily awake at a predetermined time can be executed at appropriate timing.

Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
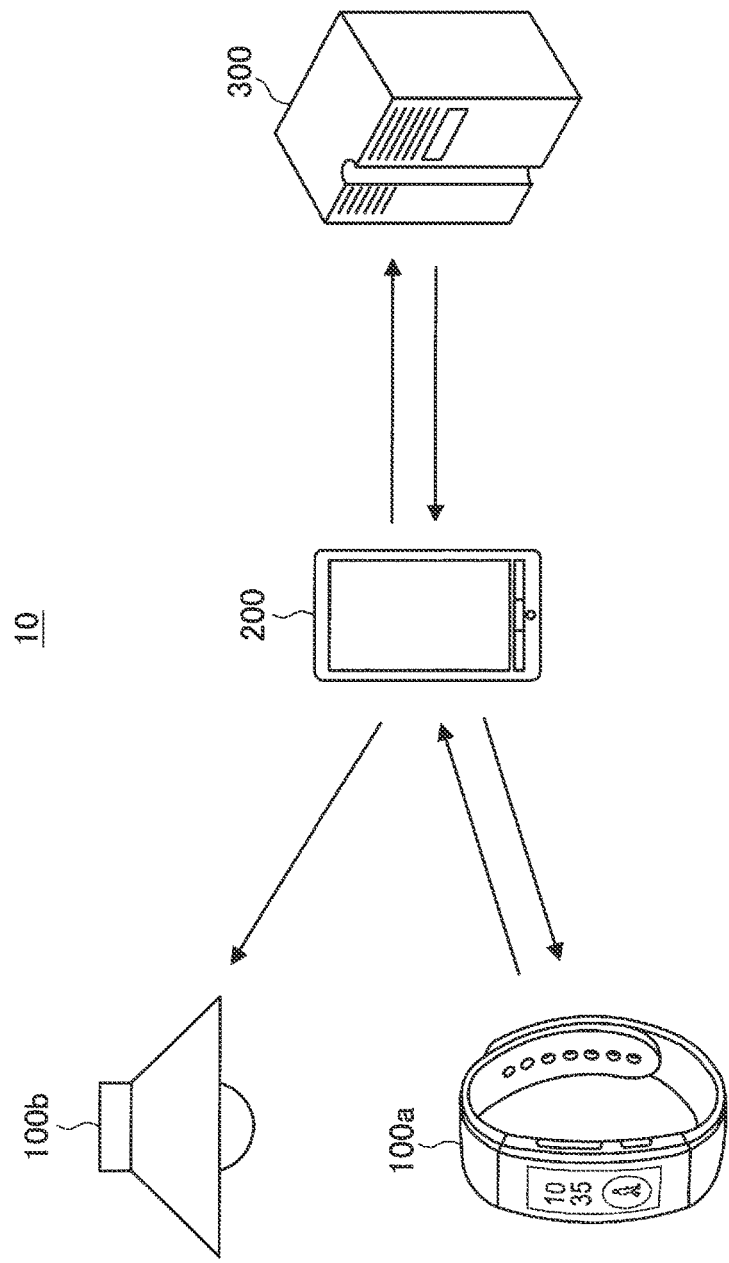
FIG. 1 is a view schematically illustrating a configuration of a system according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that description will be provided in the following order.
1. System configuration
2. Examples of changing transition of depth of sleep
3. Utilization of information on similar user
4. Examples of user interface
5. Hardware configuration
6. Supplement (1. System Configuration)

FIG. 1 is a view schematically illustrating a configuration of a system according to an embodiment of the present disclosure. In the example illustrated in FIG. 1, a system 10 includes a wearable terminal 100*a*, a lighting device 100*b*, a mobile terminal 200, and a server 300. Note that the present embodiment relates to a service provided in the system 10 for changing the sleeping environment on the basis of the depth of sleep of a user. Therefore, description of other functions that respective structural elements of the system 10 have will be omitted in the following description.

The wearable terminal 100*a* is illustrated in the drawing as an example of a device including a sensor that senses an indicator for measuring the depth of sleep of a user. The depth of sleep of a user is measured on the basis of a biological indicator, such as body temperature, pulse, respiration, or blood elements, for example. Alternatively, the depth of sleep may also be measured on the basis of an indicator other than a biological indicator, such as a user's body motion indicated by acceleration, for example. The wearable terminal 100*a* includes various sensors for sensing an indicator as described above, for example. A sensed value of the sensor is transmitted to the mobile terminal 200 upon preprocessing according to necessity. The wearable terminal 100*a* may further include a sensor that senses an indicator for measuring the sleeping environment of a user. The sleeping environment of a user is measured on the basis of an indicator, such as temperature, humidity, or sound, for example.

The lighting device 100*b* is illustrated in the drawing as an example of a device having a function of changing the sleeping environment of a user. The sleeping environment of a user includes, as elements, room brightness, temperature, humidity, sound, and vibrations, for example. The lighting device 100*b* has a function of changing the room brightness among them. The system 10 may include a device that changes another element of the sleeping environment in addition to or instead of the lighting device 100*b*. For example, the system 10 may include an air conditioner that changes room temperature and humidity, a speaker that generates sound, a vibrator that generates vibrations, and the like.

Note that, in the illustrated example, the sleeping environment of a user can also be changed by the wearable terminal 100*a* or the mobile terminal 200, for example, not limited to the lighting device 100*b*. More specifically, for example, the wearable terminal 100*a* or the mobile terminal 200 may include a speaker or a vibrator as an output apparatus, and may change the sleeping environment of a user by outputting sound or vibrations using them. In this manner, in the present embodiment, structural elements of the system 10 illustrated in FIG. 1 as the wearable terminal 100*a*, the lighting device 100*b*, and the mobile terminal 200 may not necessarily be devices independent of one another, but functions of a plurality of structural elements may be integrated into a common device.

The mobile terminal 200 has a function of communicating with the wearable terminal 100*a* and the lighting device 100*b*, a function of communicating with the server 300, an information processing function, and an information presenting function. The mobile terminal 200 and the wearable terminal 100*a* communicate by Bluetooth (registered trademark), for example. Moreover, the mobile terminal 200 and the lighting device 100*b* communicate via a home local area network (LAN) or the like, for example. The mobile terminal 200 and the server 300 communicate via the Internet or the like, for example. For example, the mobile terminal 200 receives a sensed value of the sensor from the wearable terminal 100*a*, and transfers this to the server 300 upon processing according to necessity. Furthermore, for example, the mobile terminal 200 receives information about a change in the sleeping environment of a user from the server 300, and transfers this to the lighting device 100*b* and/or the wearable terminal 100*a* upon processing according to necessity.

Further, in the present embodiment, the mobile terminal 200 may have a function of presenting information to a user via an output apparatus such as a display and a function of accepting a user operational input via an input apparatus such as a touch panel. These functions are utilized in a service that changes the sleeping environment on the basis of the depth of sleep of a user. More specifically, the mobile terminal 200 may be used to present to a user how the sleeping environment of the user has been changed and to acquire feedback in response to this from the user. Note that specific examples of presented information and acquired feedback will be described later.

The server 300 is achieved by one or a plurality of information processing devices over a network. The server 300 provides a user with a service via the mobile terminal 200, the wearable terminal 100*a*, and the lighting device 100*b*. More specifically, the server 300 measures the depth of sleep on the basis of a sensed value of the sensor (indicating user's body temperature, pulse, respiration, blood elements, and/or acceleration, etc., for example) received from the wearable terminal 100*a* via the mobile terminal 200, and decides how to change the sleeping environment of the user on the basis of the measured depth of sleep. Furthermore, the server 300 transmits information for changing the sleeping environment of the user to the lighting device 100*b* and/or the wearable terminal 100*a* via the mobile terminal 200. Note that a specific exemplary process of deciding how to change the sleeping environment on the basis of the measured depth of sleep will be described later.

In the system 10 as described above, it is possible to distribute the functions of the server 300, for example, among the mobile terminal 200, the wearable terminal 100*a*, or the lighting device 100*b*. For example, the mobile terminal 200 may measure the depth of sleep on the basis of a sensed value of a sensor in place of the server 300. Furthermore, the mobile terminal 200 may decide how to change the sleeping environment. In such a case, the system 10 may not include the server 300, but the process may be completed among the wearable terminal 100a, the lighting device 100b, and the mobile terminal 200.

Moreover, in such a case where the wearable terminal 100a has a high information processing capacity, for example, the wearable terminal 100a itself may measure the depth of sleep on the basis of a sensed value of a sensor, and may transmit the measured depth of sleep to the mobile terminal 200. In addition, the wearable terminal 100a may decide how to change the sleeping environment on the basis of the depth of sleep, and may transmit information for changing the sleeping environment to the lighting device 100b via the mobile terminal 200. In this case, the mobile terminal 200 may not be involved in a substantial process, but the process of the system 10 may be completed between the wearable terminal 100a and the lighting device 100b. Furthermore, in such a case where the wearable terminal 100a itself changes the sleeping environment of a user using a speaker or a vibrator included as an output apparatus, the system 10 may complete within the wearable terminal 100a. In this manner, in the system 10 for achieving the present embodiment, the functions can be integrated, distributed, or the like within a range that is clear to those skilled in the art irrespective of the example of FIG. 1.

In the system 10 described above, individual information processing devices constituting the mobile terminal 200 and the server 300 may each be achieved by a hardware configuration of an information processing device which will be described later. The wearable terminal 100a and the lighting device 100b may also be achieved by the hardware configuration of the information processing device which will be described later as long as they have an information processing function. However, as to these devices, in such a case where a substantial information processing device is not implemented, for example, each of the devices may be achieved by a more simplified circuit configuration, such as by achieving the wearable terminal 100a by a sensor and a communication circuit and achieving the lighting device 100b by a lighting control circuit and a communication circuit. In such a case, a configuration that is clear to those skilled in the art as a wearable sensor or a network-connected lighting device, for example, can be adopted as a hardware configuration of each of the devices.

Figure 2:
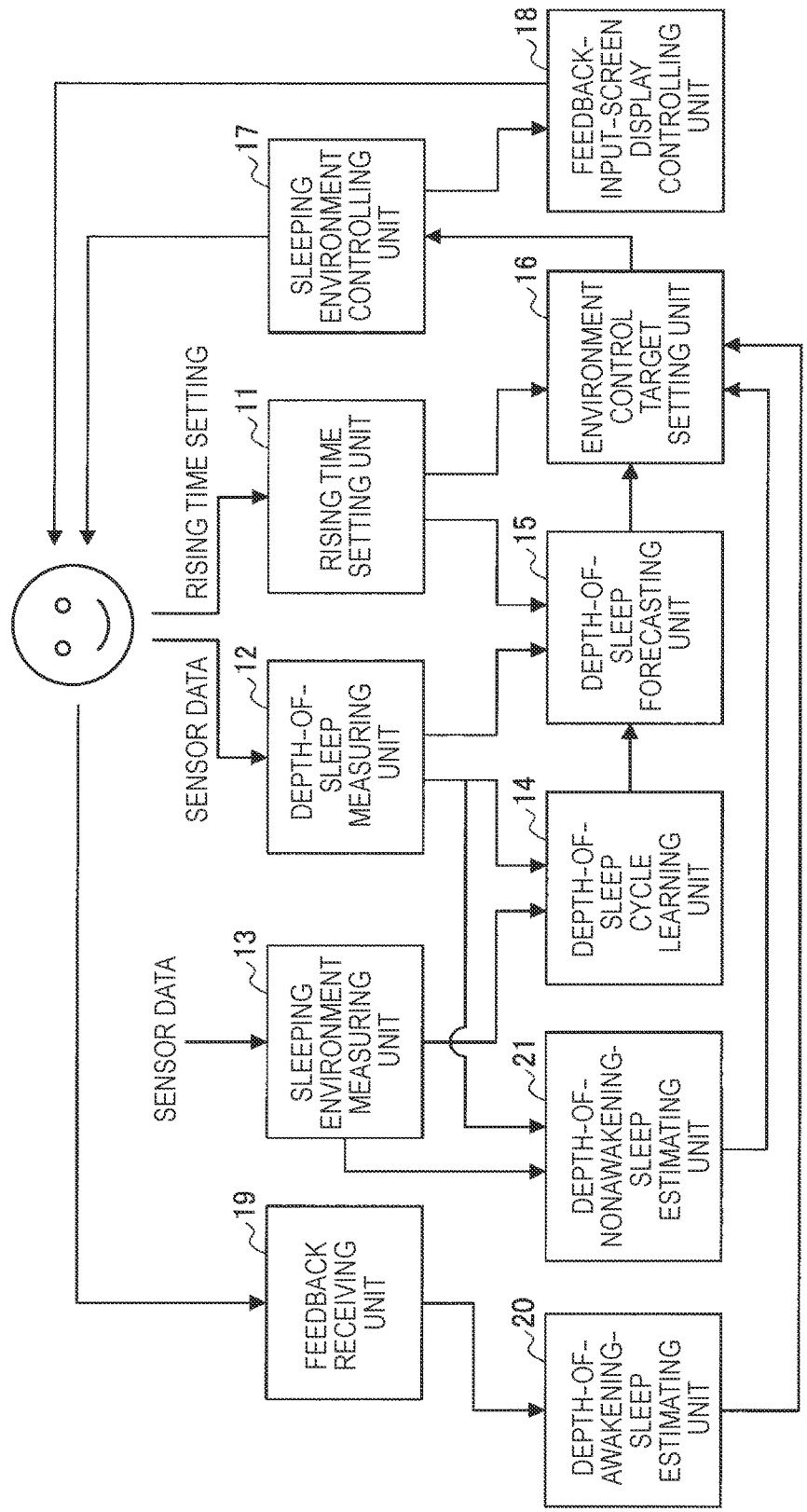
FIG. 2 is a block diagram illustrating a functional component of the system according to an embodiment of the present disclosure.

FIG. 2 is a block diagram illustrating functional components of the system according to an embodiment of the present disclosure. In FIG. 2, a rising time setting unit 11 to a depth-of-nonawakening-sleep estimating unit 21 are shown as functional components of the system 10. These functional components are achieved by a processor such as CPU operating in accordance with a program in the wearable terminal 100a, the lighting device 100b, the mobile terminal 200, or the server 300 illustrated in FIG. 1 described above, for example. Note that an exemplary device in which the respective functional components are achieved may be shown in the following description, whilst those functional components may also be achieved by another device in the system 10 irrespective of the described example.

The rising time setting unit 11 accepts setting of a user-desired rising time. More specifically, for example, the rising time setting unit 11 is implemented as a program module that accepts a setting operational input of a rising time by means of an input apparatus, such as a touch panel, included in the mobile terminal 200 or the wearable terminal 100a. The rising time setting unit 11 is implemented in a device (for example, the mobile terminal 200 or the wearable terminal 100a) that accepts a setting operational input or a device (for example, the mobile terminal 200 or the server 300) that receives contents of a setting operational input from another device.

A depth-of-sleep measuring unit 12 measures the depth of sleep of a user. More specifically, for example, the depth-of-sleep measuring unit 12 is implemented as a program module that accepts sensor data acquired by a sensor included in the wearable terminal 100a, and on the basis of this, measures the depth of sleep. The depth-of-sleep measuring unit 12 is implemented in a device including a sensor (for example, the wearable terminal 100a) or a device that receives sensor data (for example, the mobile terminal 200 or the server 300). Note that, as to a method of measuring the depth of sleep of a user on the basis of a biological indicator (body temperature, pulse, respiration, blood elements, or the like) or another indicator (acceleration indicating a body motion or the like) included in the sensor data, various publicly-known techniques can be utilized. The depth-of-sleep measuring unit 12 stores the measured depth of sleep in a memory or a storage as time series data.

A sleeping environment measuring unit 13 measures the sleeping environment of the user. More specifically, for example, the sleeping environment measuring unit 13 is implemented as a program module that accepts sensor data acquired by the sensor included in the wearable terminal 100a, and on the basis of this, measures the sleeping environment. The sleeping environment measuring unit 13 is implemented in a device including a sensor or a device that receives sensor data, similarly to the depth-of-sleep measuring unit 12 described above. Note that, as to a method of measuring the sleeping environment of the user on the basis of various indicators included in sensor data, various publicly-known techniques can be utilized. The sleeping environment measuring unit 13 stores the measured sleeping environment in a memory or a storage as time series data.

Figure 3:
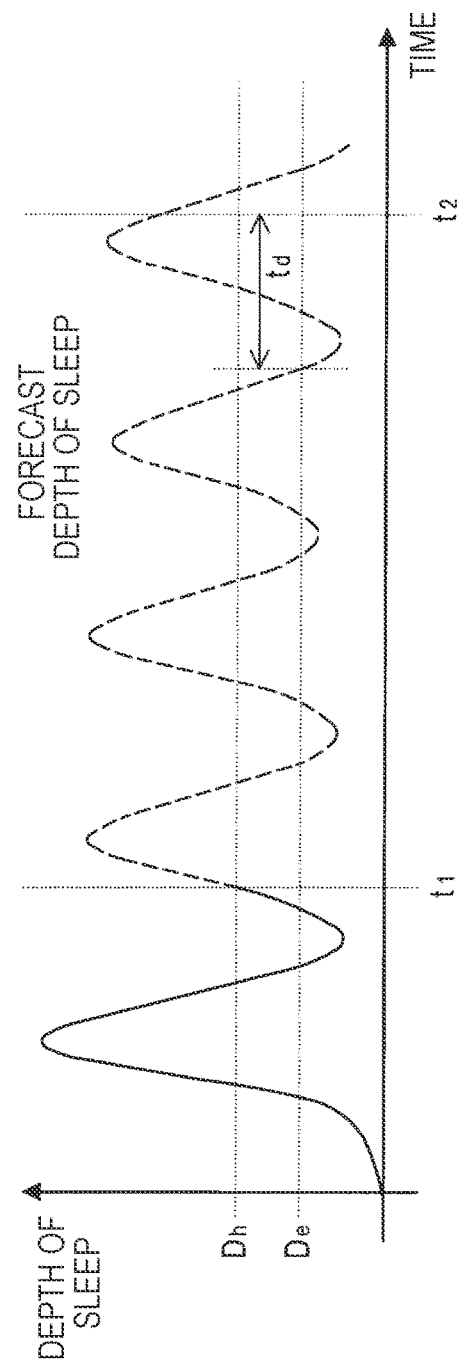
FIG. 3 is a view illustrating an exemplary transition of a depth of sleep after a certain time forecast on the basis of a depth of sleep of a user measured by the certain time in an embodiment of the present disclosure.

A depth-of-sleep cycle learning unit 14 executes machine learning on the basis of the time series data on the depth of sleep of the user measured by the depth-of-sleep measuring unit 12 and the sleeping environment of the user measured by the sleeping environment measuring unit 13, and estimates a varying cycle of the depth of sleep of the user. The depth of sleep of the user is known to vary periodically in many cases as illustrated in FIG. 3, for example. Therefore, if the varying cycle of the depth of sleep can be estimated by learning, a transition of the depth of sleep of the user can be forecast as in processing of a depth-of-sleep forecasting unit 15 which will be described later. As described above, in the present embodiment, the varying cycle of the depth of sleep of the user is estimated on the basis of time series data on the depth of sleep of the user actually measured by the depth-of-sleep measuring unit 12, that is, transition performance of the depth of sleep.

Here, the varying cycle of the depth of sleep of a user may be different depending on the sleeping environment, for example. Therefore, the depth-of-sleep cycle learning unit 14 may carry out learning merely on the basis of time series data on the depth of sleep, or may improve the accuracy of estimation by further carrying out learning on the basis of time series data on the sleeping environment. Note that, in the present embodiment, the transition of the depth of sleep of the user only needs to be forecastable as a result of learning, and its technique is not necessarily limited to estimating the varying cycle of the depth of sleep. Therefore, in another example, another temporal pattern of the depth of sleep may be extracted in order to forecast the transition of the depth of sleep. A cyclical variation of the depth of sleep as described above is an exemplary temporal pattern of the transition of the depth of sleep.

The depth-of-sleep forecasting unit 15 forecasts the transition of the depth of sleep of the user on the basis of the depth of sleep of the user measured by the depth-of-sleep measuring unit 12, the sleeping environment of the user measured by the sleeping environment measuring unit 13, and the cycle of the depth of sleep estimated by the depth-of-sleep cycle learning unit 14 on the basis of the result of learning. More specifically, the depth-of-sleep forecasting unit 15 forecasts the transition of the depth of sleep of the user at least in a period from a first time $t_1$ to a second time $t_2$, as illustrated in FIG. 3, for example. Here, the second time $t_2$ may be, for example, a user-desired rising time whose setting has been accepted by the rising time setting unit 11.

Here, in a case where the depth-of-sleep cycle learning unit 14 carries out leaning also on the basis of time series data on the sleeping environment of the user provided by the sleeping environment measuring unit 13, the depth-of-sleep forecasting unit 15 forecasts the transition of the depth of sleep of the user after the first time $t_1$ also on the basis of the sleeping environment of the user measured by the first time $t_1$ by the sleeping environment measuring unit 13. At this time, the depth-of-sleep forecasting unit 15 may regard that the sleeping environment after the first time $t_1$ does not change or changes in accordance with a predetermined pattern (for example, the room temperature gradually approaches the outside temperature in a case where an air conditioner has not been activated, or the room brightness changes in accordance with the sunshine state in a case where a lighting device has not been activated). Alternatively, the depth-of-sleep forecasting unit 15 may acquire setting information of an air conditioner, a lighting device, or the like to forecast the transition of the sleeping environment on the basis of them, and may forecast the transition of the depth of sleep on the basis of the forecast sleeping environment.

On the basis of the result of forecast by the depth-of-sleep forecasting unit 15, an environment control target setting unit 16 determines whether the depth of sleep of the user at the second time $t_2$ (in this example, the user-desired rising time) falls within a range suitable for awakening, and in a case where the forecast depth of sleep does not fall within the range suitable for awakening, sets an environment control target such that the forecast depth of sleep falls within the range suitable for awakening.

For example, in the case illustrated in FIG. 3, the forecast depth of sleep at the second time $t_2$ exceeds a depth of sleep $D_e$ (hereinafter, also referred to as a first depth-of-sleep threshold value) estimated as the upper limit of a depth-of-sleep region in which the user is likely to awake (hereinafter, also referred to as a first depth-of-sleep region or a depth-of-awakening-sleep region). Therefore, the environment control target setting unit 16 sets a target of sleeping environment control such that the depth of sleep of the user at the second time $t_2$ falls below the first depth-of-sleep threshold value $D_e$. Note that it is assumed in the present specification that the value of the depth of sleep increases as sleep is deepened.

In the above-described case, if the transition of the depth of sleep can be delayed by a time $t_d$ by changing the sleeping environment between the first time $t_1$ and the second time $t_2$, for example, the forecast depth of sleep at the second time $t_2$ will fall below the depth of sleep $D_e$ to enter the depth-of-awakening-sleep region. In this case, the environment control target setting unit 16 sets delaying the transition of the depth of sleep by the time $t_d$ between the first time $t_1$ and the second time $t_2$ as the target of sleeping environment control. In this case, a control method of producing a delay in the transition of the depth of sleep is selected in sleeping environment control. In another example, the environment control target setting unit 16 may set changing the varying cycle of the depth of sleep as the target of sleeping environment control, and a control method of producing a change in the varying cycle of the depth of sleep may be selected.

A sleep environment controlling unit 17 controls the sleeping environment of the user such that the target set by the environment control target setting unit 16 is attained. As described above, in the present embodiment, the sleeping environment of the user includes, as elements, room brightness, temperature, humidity, sound, vibrations, and the like, for example. Such elements of the sleeping environment can be changed by, for example, the lighting device 100b that changes room brightness, an air conditioner that changes room temperature or humidity, a speaker that generates sound, a vibrator that generates vibrations, or the like. Therefore, in the present embodiment, the sleep environment controlling unit 17 can change the sleeping environment of the user by controlling the lighting device 100b, air conditioner, speaker, and/or vibrator, for example. Note that it can be decided by utilizing various publicly-known techniques as to which of available controlled means (for example, the lighting device 100b, air conditioner, speaker, and/or vibrator) the sleep environment controlling unit 17 uses and to what degree the sleeping environment of the user is changed in order to attain the target set by the environment control target setting unit 16. The sleep environment controlling unit 17 may decide the type of such sleeping environment control in accordance with a temporal pattern of the transition of the forecast depth of sleep of the user.

Here, the sleep environment controlling unit 17 decides the temporal pattern of sleeping environment control in the period from the first time $t_1$ to the second time $t_2$ in accordance with the temporal pattern of the transition of the depth of sleep of the user forecast by the depth-of-sleep forecasting unit 15. More specifically, for example, the pattern may define that sleeping environment control is distributed among a plurality of times between the first time and the second time. Here, the above-described plurality of times may be times at which the depth of sleep of the user is forecast to exceed the lower limit value (a depth of sleep $D_h$ shown in FIG. 3; hereinafter, also referred to as a second depth-of-sleep threshold value) of a depth-of-sleep region in which the user is unlikely to awake (hereinafter, also referred to as a second depth-of-sleep region or a depth-of-nonawakening-sleep region). Alternatively, the pattern may define that the sleeping environment is continuously controlled from the first time to the second time. Note that a specific exemplary temporal pattern of sleeping environment control will be described later.

Note that the system 10 may include a functional component that provides an alarm for reliably awaking the user at the second time (user-desired rising time). Although the alarm is provided by sound output from a speaker or vibrations generated by a vibrator, for example, its method is not particularly limited, but various publicly-known alarms can be utilized. The alarm may be provided by the sleep environment controlling unit 17, or may be provided by another functional component not illustrated in the drawing. In any case, since a component for providing an alarm is publicly known, description of an alarm provided at the second time will be omitted in the following description. Therefore, even if an operation of providing an alarm at the second time is not included in the description of the operation of the sleep environment controlling unit 17, for example, it does not necessarily mean that the sleep environment controlling unit 17 does not provide an alarm.

A feedback-input-screen display controlling unit 18 executes control of displaying an input screen for the user to input feedback after the user rises. The input screen is displayed on a display of the mobile terminal 200, for example, as described above. The input screen may include information indicating that the sleeping environment control has been executed by the sleep environment controlling unit 17 before awakening, details of the executed control, and the like, as well as an element for inputting a user's impression at awakening (whether it was easy to awake, it was hard to awake, or the like), for example. In another example, information for having feedback input may not necessarily be displayed on the display, but may be output by sound, for example.

A feedback receiving unit 19 receives feedback given by the user on the input screen displayed in accordance with the control by the feedback-input-screen display controlling unit 18. The feedback is acquired via an input apparatus such as a touch panel provided on the display that displays the input screen or operation buttons, for example. Alternatively, the feedback may be acquired as sound through a microphone included in the mobile terminal 200, the wearable terminal 100a, or the like. In this case, the acquired feedback may be information indicating a user's impression at awakening and the like.

Moreover, the feedback receiving unit 19 may acquire, as feedback, sensed values of the sensor included in the wearable terminal 100a (indicating user's body temperature, pulse, respiration, blood elements, and/or acceleration, etc., for example), in addition to or instead of the feedback by a user's operational input, sound, or the like. As described above, these sensed values are utilized for measuring the depth of sleep of the user, but can also be utilized as user feedback on an alarm at awakening and the like.

A depth-of-awakening-sleep estimating unit 20 estimates a depth-of-sleep region in which the user is likely to awake (the above-described depth-of-awakening-sleep region) on the basis of the feedback received by the feedback receiving unit 19. More specifically, the depth-of-awakening-sleep estimating unit 20 estimates a first depth-of-sleep threshold value (shown as the depth of sleep $D_e$ in the example of FIG. 3) estimated as the upper limit of the depth-of-awakening-sleep region. In the present embodiment, the depth-of-awakening-sleep estimating unit 20 carries out estimation on the basis of feedback acquired after the user awakes. For example, the feedback includes an impression at awakening indicated by a user's operational input or sound input. In this case, the depth-of-awakening-sleep estimating unit 20 estimates that the depth of sleep of the user before awakening in a case where it is indicated by feedback that a user's impression at awakening was good (awoke comfortably) falls below the first depth-of-sleep threshold value. In addition, for example, the feedback includes sensor data, such as biological information, acquired by a sensor after the user awakes. In this case, the depth-of-awakening-sleep estimating unit 20 estimates that the depth of sleep of the user before awakening in a case where it is indicated by sensor data that the user's activity after awakening was high falls below the first depth-of-sleep threshold value.

The depth-of-nonawakening-sleep estimating unit 21 estimates a depth-of-sleep region in which the user is unlikely to awake (the above-described depth-of-nonawakening-sleep region) on the basis of a result of exerting sleeping environment control on the user. More specifically, the depth-of-nonawakening-sleep estimating unit 21 estimates a second depth-of-sleep threshold value (shown as the depth of sleep $D_h$ in the example of FIG. 3) estimated as the lower limit of the depth-of-nonawakening-sleep region. For example, in a case where the user unintentionally awakes when the sleeping environment control is executed by the sleep environment controlling unit 17 (a failure as the sleeping environment control), the depth-of-nonawakening-sleep estimating unit 21 estimates that the depth of sleep when the sleeping environment control is executed falls below the second depth-of-sleep threshold value and is not included in the depth-of-nonawakening-sleep region. Note that it is recognized that the user has awaken from the result of measurement of the depth of sleep by the depth-of-sleep measuring unit 12, for example. In contrast, in a case where the user continues sleeping even after the sleeping environment control is executed by the sleep environment controlling unit 17, the depth-of-nonawakening-sleep estimating unit 21 estimates that the depth of sleep when the sleeping environment control is executed exceeds the second depth-of-sleep threshold value and is included in the depth-of-nonawakening-sleep region.

The ranges of the depth of sleep respectively estimated by the depth-of-awakening-sleep estimating unit 20 and the depth-of-nonawakening-sleep estimating unit 21 described above are utilized for processing in the environment control target setting unit 16 and the sleep environment controlling unit 17. For example, in the example illustrated in FIG. 3, the environment control target setting unit 16 sets the target of sleeping environment control such that the forecast depth of sleep is included in the range of depth of awakening sleep (which falls below the depth of sleep $D_e$) at the second time $t_2$ (user-desired rising time). Moreover, the sleep environment controlling unit 17 decides at which time between the first time $t_1$ and the second time $t_2$ to execute control for changing the sleeping environment, in accordance with the relationship between the depth of sleep and the second depth-of-sleep threshold value $D_h$. More specifically, for example, the sleep environment controlling unit 17 executes the sleeping environment control at a time when the depth of sleep is forecast to exceed the depth of sleep $D_h$.

(2. Examples of Changing Transition of Depth of Sleep)

Figure 4:
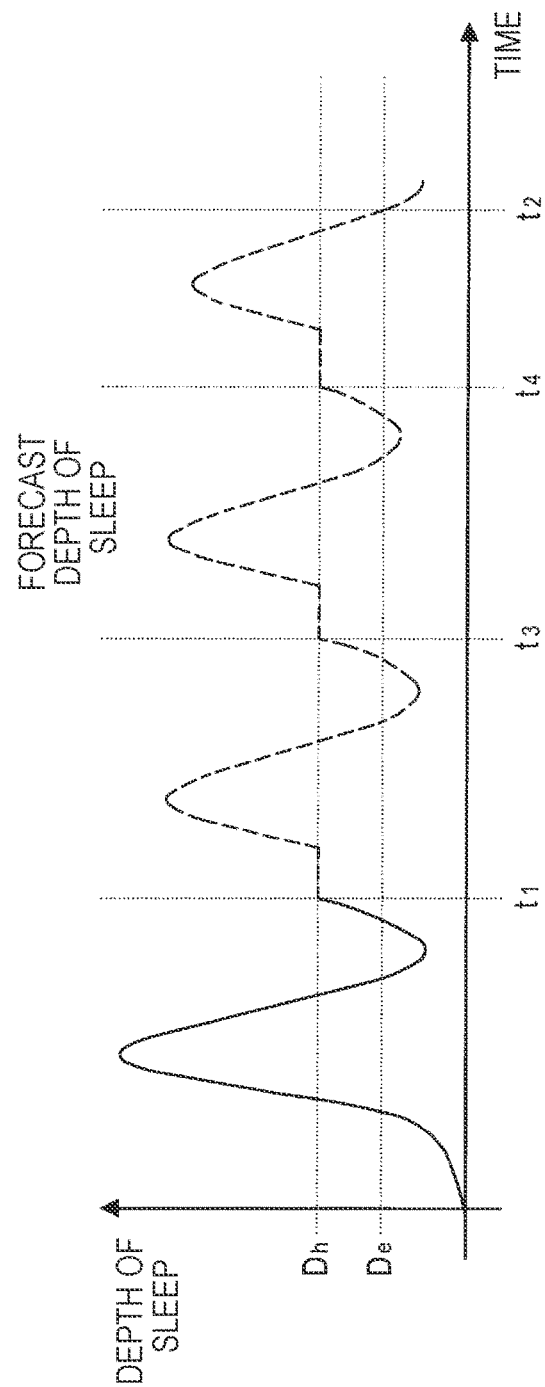
FIG. 4 is a view illustrating a first example of changing the transition of the depth of sleep in the example of FIG. 3.
Figure 5:
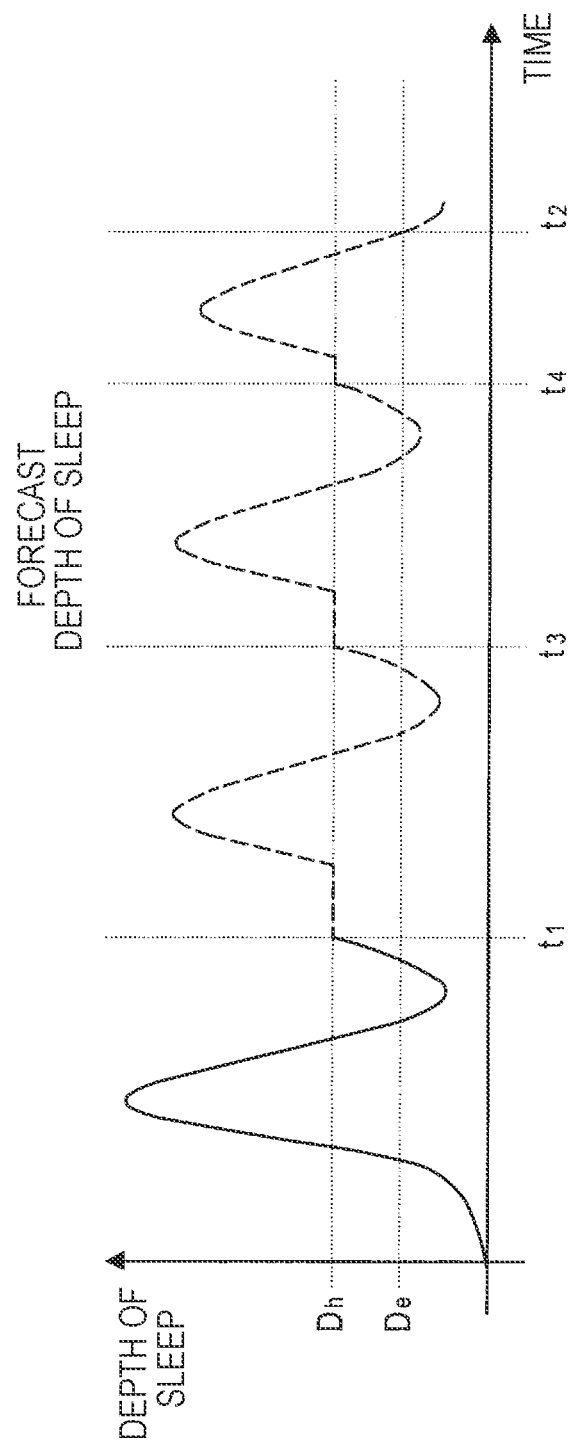
FIG. 5 is a view illustrating a second example of changing the transition of the depth of sleep in the example of FIG. 3.
Figure 6:
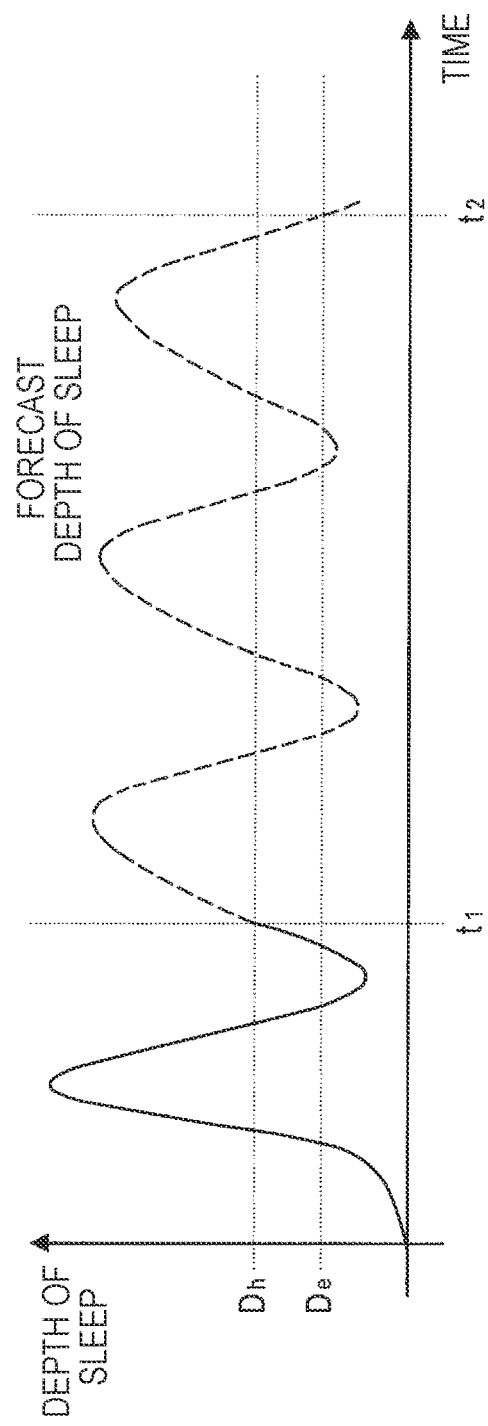
FIG. 6 is a view illustrating a third example of changing the transition of the depth of sleep in the example of FIG. 3.

FIG. 3 to FIG. 6 are views for conceptually describing examples of changing the transition of the depth of sleep in an embodiment of the present disclosure. More specifically, FIG. 3 illustrates an exemplary transition of the depth of sleep forecast at a certain time (the first time $t_1$) in an embodiment of the present disclosure. FIG. 4 to FIG. 6 are views illustrating first to third examples of changing the transition of the depth of sleep in the example of FIG. 3.

As already described, in FIG. 3, the transition of the depth of sleep in the period from the first time $t_1$ to the second time $t_2$ is forecast by the depth-of-sleep forecasting unit 15 on the basis of the result of learning in the depth-of-sleep cycle learning unit 14 included in the system 10. Here, the temporal pattern of the forecast transition of the depth of sleep includes cyclical variations of the depth of sleep across the depth of sleep $D_h$ estimated as the lower limit of the depth-of-nonawakening-sleep region. In accordance with this forecast, the depth of sleep at the second time $t_2$ (user-desired rising time) exceeds the depth of sleep $D_e$, and the user may not be able to awake smoothly. Therefore, the environment control target setting unit 16 sets, as the target of sleeping environment control, delaying the transition of the depth of sleep of the user by the time $t_d$ between the first time $t_1$ and the second time $t_2$ so that the forecast depth of sleep at the second time $t_2$ becomes a depth of awakening sleep that falls below the depth of sleep $D_e$.

FIG. 4 is a view illustrating the first example of executing the sleeping environment control distributed among three times from the first time $t_1$ to the second time $t_2$ (including the time $t_1$) in the example of FIG. 3. Here, each of the times $t_1$, $t_3$, and $t_4$ at which the sleeping environment control is executed in the example illustrated in FIG. 4 is a time point at which the depth of sleep or the forecast depth of sleep exceeds the depth of sleep $D_h$ to enter the range of the depth of nonawakening sleep. This is for preventing the user from awaking unintentionally due to a change in the sleeping environment. For example, in a case where delaying the transition of the depth of sleep by the time $t_d$ is a target, the sleeping environment control is distributed equally in the example illustrated in the drawing, and control for changing the sleeping environment is executed such that the transition of the depth of sleep is delayed by $t_d/3$ at each of the three times $t_1$, $t_3$, and $t_4$.

Note that illustrated in FIG. 4 are a pattern of changes in sleeping environment decided at the time point of the time $t_1$ and a forecast on the transition of the depth of sleep in a case where the sleeping environment has changed in accordance with the pattern. Therefore, the sleeping environment may be changed actually after the time $t_1$, and as time advances, an actual transition of the depth of sleep may be different from the illustrated forecast. For such a case, when the times $t_3$ and $t_4$ at which the second and subsequent changes in sleeping environment are executed approach, again, the depth-of-sleep measuring unit 12 may measure the depth of sleep of the user, the depth-of-sleep forecasting unit 15 may forecast the transition of the depth of sleep of the user, the environment control target setting unit 16 may set a target of environment control, and the sleep environment controlling unit 17 may decide a pattern in which the sleeping environment is changed in accordance with the target.

More specifically, for example, when a change in sleeping environment is executed such that the transition of the depth of sleep is delayed by $t_d/3$ at the time $t_1$, and then the transition of the depth of sleep is forecast again at the time $t_3$ as described above, and in a case where the influence of the change in sleeping environment has not appeared sufficiently, and the transition of the depth of sleep has been expedited by a time $\Delta t$ with respect to the forecast at the time $t_1$ illustrated in FIG. 4 (that is, although the target was a delay by the time $t_d$, a delay will be made only by the time $t_d-\Delta t$ as it is), the sleep environment controlling unit 17 executes control for changing the sleeping environment so as to delay the transition of the depth of sleep by $t_d/3+\Delta t/2$ at each of the times $t_3$ and $t_4$. Similarly, at the time $t_4$ as well, by forecasting the transition of the depth of sleep again and correcting the pattern in which the sleep environment controlling unit 17 changes the sleeping environment, the depth of sleep of the user at the second time $t_2$ can be guided more reliably to be a depth of awakening sleep that falls below the depth of sleep $D_e$.

FIG. 5 is a view illustrating the second example of executing the sleeping environment control distributed among three times from the first time $t_1$ to the second time $t_2$ (including the time $t_1$) in the example of FIG. 3. In the example illustrated in the drawing, similarly to the above-described example illustrated in FIG. 4, sleeping environment control for delaying the transition of the depth of sleep is executed in a manner distributed among the times $t_1$, $t_3$, and $t_4$ at which the depth of sleep or the forecast depth of sleep exceeds the depth of sleep $D_h$ to enter the range of the depth of nonawakening sleep. As a difference from the example of FIG. 4, changes in sleeping environment is distributed unequally among the three times $t_1$, $t_3$, and $t_4$ in the example of FIG. 5. More specifically, for example, in the example illustrated in the drawing, control for changing the sleeping environment is executed so as to delay the transition of the depth of sleep by $t_d/2$ at the time $t_1$, by $t_d/3$ at the time $t_3$, and by $t_d/6$ at the time $t_4$, respectively.

In this manner, in such a case of unequally distributing changes in sleeping environment among a plurality of times, the changes in sleeping environment can be distributed at a higher ratio at a time closer to the time $t_1$ (including the time $t_1$ itself), for example. For example, in such a case where an error is expected to occur in the influence on the transition of the depth of sleep due to the changes in sleeping environment, a large change in sleeping environment that exerts a larger influence on the transition of the depth of sleep is given at the time $t_1$, so that a moderate change in sleeping environment can be given at the time $t_3$ in consideration of an error in the influence caused by the initial change in sleeping environment, and a minimum change in sleeping environment for adjusting a still remaining error can be given at the time $t_4$. Assuming that an error that would occur is smaller as the degree of changes in sleeping environment is smaller, the influence of an error can be minimized by an unequal distribution of changes in sleeping environment as described above to guide more reliably the depth of sleep of the user at the second time $t_2$ to be a depth of awakening sleep that falls below the depth of sleep $D_e$.

Note that the above-described example of sleeping environment control illustrated in FIG. 4 and the similar example illustrated in FIG. 5 are used properly as necessary depending on the degree of error occurred in the influence on the transition of the depth of sleep due to changes in sleeping environment, the possibility of an unexpected change (such as awakening of the user) due to changes in sleeping environment, or the like, for example. More specifically, for example, in such a case where an error is expected to occur in the influence on the transition of the depth of sleep due to changes in sleeping environment as described above, changes in sleeping environment may be distributed unequally among a plurality of times as in the example illustrated in FIG. 5 so that the transition of the depth of sleep can be adjusted with a smaller change in sleeping environment at a later time. In addition, in such a case where the user could be awaken by continuing changing the sleeping environment for a long time (even in the depth of nonawakening sleep), for example, changes in sleeping environment may be distributed equally among a plurality of times as illustrated in FIG. 4 to equally minimize a change in sleeping environment at each of the times.

FIG. 6 is a view illustrating an example of executing the sleeping environment control continuously from the first time $t_1$ to the second time $t_2$ in the example of FIG. 3. In the example illustrated in the drawing, the varying cycle of the depth of sleep is extended by continually controlling the sleeping environment unlike the examples described above with reference to FIG. 4 and FIG. 5, and as a result, the forecast depth of sleep at the second time $t_2$ falls below the depth of sleep $D_e$. For example, in a case where it is possible to change the varying cycle of the depth of sleep as illustrated in the drawing instead of delaying the transition of the depth of sleep of the user by changing the sleeping environment (in a case where means for changing the sleeping environment in such a manner is available), changes in sleeping environment may be slowed down by executing the sleeping environment control as in the example illustrated in FIG. 6 to allow the user to sleep comfortably until the user awakes.

Figure 7:
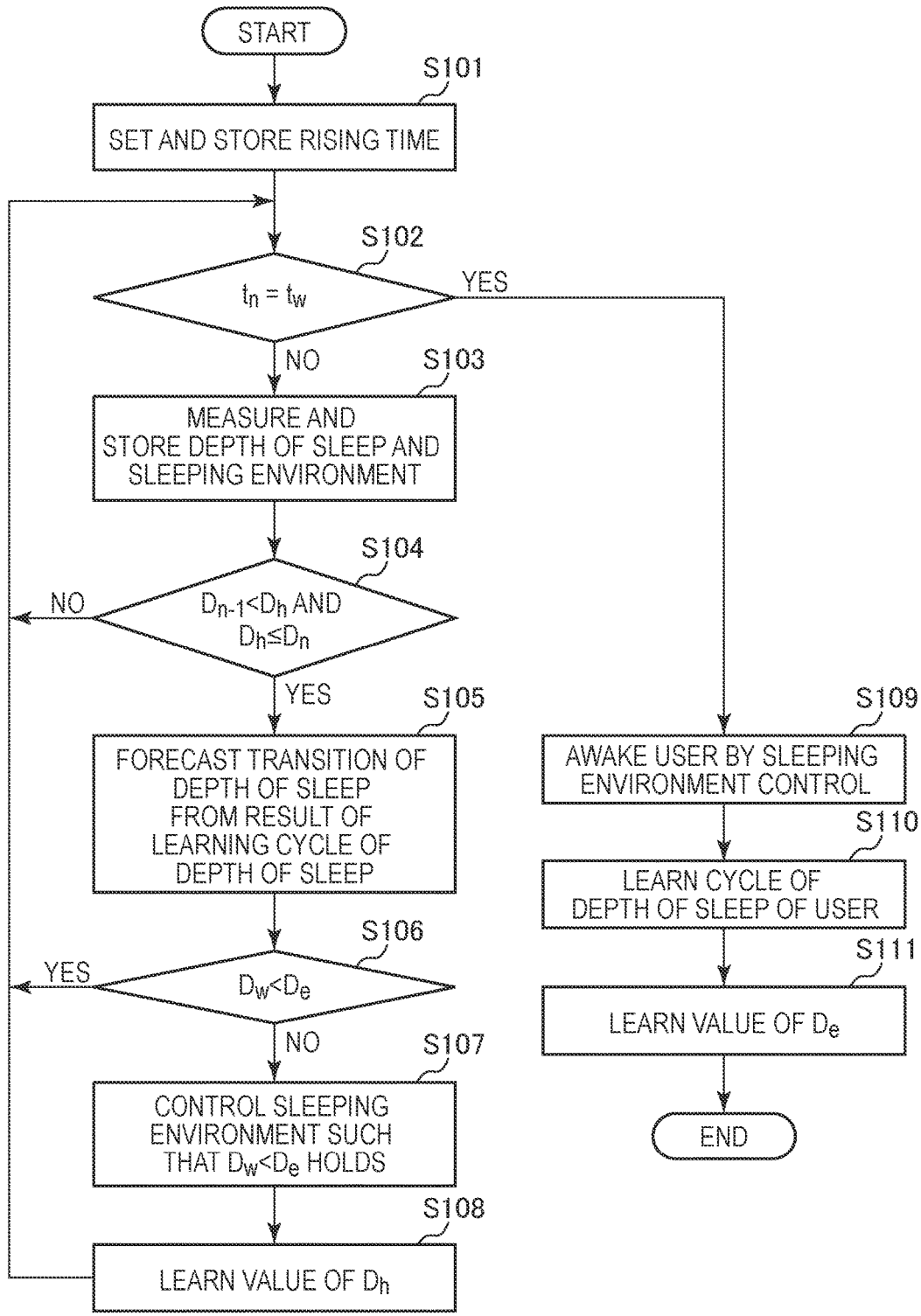
FIG. 7 is a flowchart illustrating an exemplary process for changing the transition of the depth of sleep in an embodiment of the present disclosure.

FIG. 7 is a flowchart illustrating an exemplary process for changing the transition of depth of sleep in an embodiment of the present disclosure. In the following description, a current time (the first time) is denoted by $t_n$, a set rising time (the second time) is denoted by $t_w$, a current depth of sleep is denoted by $D_n$, and the forecast depth of sleep at the rising time is denoted by $D_w$. In addition, the depth of sleep $D_h$ and the depth of sleep $D_e$ are similar to those described above with reference to FIG. 3 and the like.

First, the rising time setting unit 11 accepts a setting of a user-desired rising time, and stores this in a memory or storage (S101). Next, a functional component that provides an alarm (not explicitly illustrated in FIG. 2) determines whether the current time $t_n$ arrives at the rising time $t_w$ (S102). Here, if the current time $t_n$ is not the rising time $t_w$ (NO), the depth-of-sleep measuring unit 12 measures the depth of sleep of the user, and the sleeping environment measuring unit 13 measures the sleeping environment of the user. The depth of sleep and the sleeping environment as measured are stored in the memory or storage as time series data (S103).

Next, the depth-of-sleep forecasting unit 15 determines whether the current depth of sleep $D_n$ exceeds the depth of sleep $D_h$ estimated as the lower limit value of the depth of nonawakening sleep and whether the preceding depth of sleep $D_{n-1}$ falls below the depth of sleep $D_h$ (S104). That is, this determination is a determination as to whether the current time $t_n$ is a time point at which the depth of sleep $D_n$ exceeds the depth of sleep $D_h$ to enter the range of the depth of nonawakening sleep. Therefore, in a case where the preceding depth of sleep $D_{n-1}$ has already entered the depth of nonawakening sleep ($D_{n-1} \geq D_h$), a result of determination in S104 is NO. In this case, the process proceeds into the determination in S101 described above at a next time.

In a case where the result of determination in S104 described above is YES, the depth-of-sleep forecasting unit 15 forecasts the transition of the depth of sleep of the user after the current time $t_n$ on the basis of the result of learning of the cycle of the depth of sleep until then by the depth-of-sleep cycle learning unit 14 (S105). As described above, in addition to the result of learning of the cycle of the depth of sleep, the depth of sleep of the user measured by the current time $t_n$ by the depth-of-sleep measuring unit 12 and the sleeping environment of the user measured by the sleeping environment measuring unit 13 are used for the forecast on the transition of the depth of sleep by the depth-of-sleep forecasting unit 15.

Next, the environment control target setting unit 16 determines whether the forecast depth of sleep $D_w$ at the rising time in the result of the forecast on the transition of the depth of sleep in S105 described above falls below the depth of sleep $D_e$ estimated as the upper limit value of the depth of awakening sleep (S106). Here, in a case where the forecast depth of sleep $D_w$ falls below the depth of sleep $D_e$ (YES), it is not necessary to change the transition of the depth of sleep, and thus, the process proceeds into the determination in S101 described above at a next time. On the other hand, in a case where the forecast depth of sleep $D_w$ does not fall below the depth of sleep $D_e$ (NO), it is necessary to change the transition of the depth of sleep, and thus, the environment control target setting unit 16 proceeds into next processing of setting a target of sleeping environment control.

In this case, the environment control target setting unit 16 sets the target of sleeping environment control such that the forecast depth of sleep $D_w$ falls below the depth of sleep $D_e$. The sleep environment controlling unit 17 controls the sleeping environment of the user such that the target set here by the environment control target setting unit 16 is attained (S107). The sleeping environment control is executed in accordance with a temporal pattern decided depending on the temporal pattern of the depth of sleep between the first time (current time $t_n$) and the second time (rising time $t_w$) as in the examples described above with reference to FIG. 4 to FIG. 6, for example.

While the sleeping environment control is executed in S107 described above, the depth-of-nonawakening-sleep estimating unit 21 learns a value of the depth of sleep $D_h$ (S108). More specifically, in a case where the depth of sleep transitions as forecast in S105, for example, without the user awaking even if the sleeping environment is changed in S107, the depth-of-nonawakening-sleep estimating unit 21 can estimate that the depth of sleep $D_h$ has a value lower than the depth of sleep measured in S103. In another example, learning about the depth of nonawakening sleep may not necessarily be executed in real time, but may be executed after the user awakes along with learning of the depth of sleep in S110 which will be described later, for example, or may be executed periodically irrespective of them.

Note that the range of the depth of nonawakening sleep may be different depending on the sleeping environments before and after a change is applied in S107 (room brightness, temperature, humidity, degree of noise or vibrations, etc.) or the type of change in sleeping environment applied in S107 (whether to change the room brightness, whether to change the temperature or humidity, whether to generate sound, whether to generate vibrations, etc.), for example. Therefore, the depth-of-nonawakening-sleep estimating unit 21 may learn the depth of sleep $D_h$ in association with information on the sleeping environment measured in S103 and/or information indicating contents of the sleeping environment control in S107.

On the other hand, in a case where the current time to is the rising time $t_w$ in the determination in S103 described above (YES), a functional component that provides an alarm (not explicitly illustrated in FIG. 2) awakes the user. As described above, in the system 10, an alarm may be provided by the sleep environment controlling unit 17. In the example illustrated in FIG. 7, the user is awaken by the sleep environment controlling unit 17 controlling the sleeping environment (S109). Note that contents of the sleeping environment control executed here may be different from contents of the sleeping environment control executed in S107, for example.

After the user awakes, the depth-of-sleep cycle learning unit 14 learns the varying cycle of the depth of sleep of the user (S110). For example, in a case where a process as illustrated in FIG. 7 is continuously executed from the sleep onset to awakening of the user, time series data on the depth of sleep and the sleeping environment of the user is accumulated by the processing in S103 executed repeatedly. The depth-of-sleep cycle learning unit 14 learns the varying cycle of the depth of sleep of the user on the basis of the time series data accumulated in this manner (including transition performance of the depth of sleep). Note that learning of the varying cycle of the depth of sleep of the user may not necessarily be executed each time after the user awakes, but may be executed after sleep is repeated a predetermined times, for example. Alternatively, learning of the varying cycle of the depth of sleep of the user may be executed periodically irrespective of timing such as awakening of the user.

Furthermore, after the user awakes, the depth-of-awakening-sleep estimating unit 20 learns a value of the depth of sleep $D_e$ (S111). More specifically, in a case where it is indicated by feedback by an operational input, sound, or the like after the user awakes that an impression at awakening was good (awoke comfortably), the depth-of-awakening-sleep estimating unit 20 can estimate that the depth of sleep $D_e$ has a value higher than the depth of sleep estimated in S103 executed finally (in a usual case, the current time $t_n$ is not the rising time $t_w$ in the determination in S102 executed for the first time after setting of the rising time in S101, and S103 should be executed at least once).

Similarly, in a case where it is indicated by feedback of a detection value of a sensor that the user's activity after awakening is high, the depth-of-awakening-sleep estimating unit 20 can estimate that the depth of sleep $D_e$ has a value higher than the depth of sleep estimated in S103 executed finally. Note that the learning about the depth of awakening sleep in S111 may not necessarily be executed in real time similarly to the learning about the depth of nonawakening sleep in S108, but may be executed after sleep is repeated a predetermined times, for example, or may be executed periodically irrespective of timing such as awakening of the user.

(3. Utilization of Information on Similar User)

Figure 8:
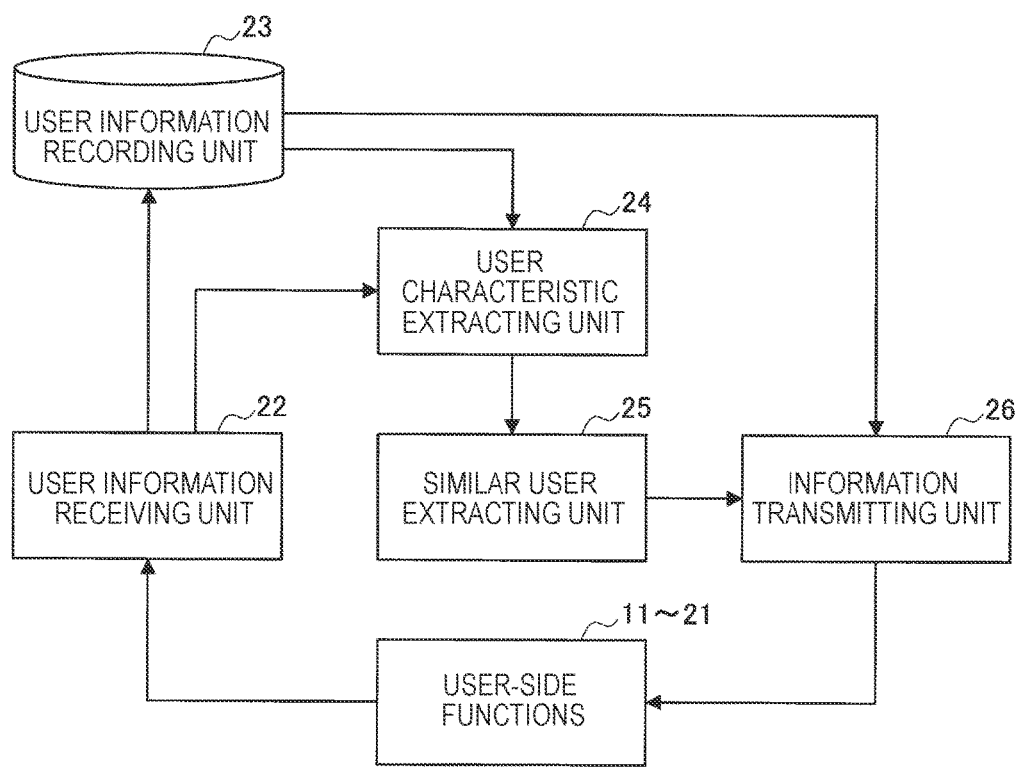
FIG. 8 is a block diagram illustrating an additional functional component for utilizing information on a similar user in the system according to an embodiment of the present disclosure.

FIG. 8 is a block diagram illustrating additional functional components for utilizing information on a similar user in the system according to an embodiment of the present disclosure. In FIG. 7, a user information receiving unit 22 to an information transmitting unit 26 are shown as additional functional components of the system 10 illustrated in FIG. 2. These functional components are achieved by a processor such as CPU operating in accordance with a program in the above-described server 300 illustrated in FIG. 1, for example. Note that, in such a case where permission for sharing information among users has been granted, for example, the above-described functional components can also be achieved by the mobile terminal 200 or the like, for example, other than the server 300.

The user information receiving unit 22 receives, from user-side functions (including the rising time setting unit 11 to the depth-of-nonawakening-sleep estimating unit 21 described above with reference to FIG. 2), information such as attribute information, such as user's age, sex, job, height, and weight, for example, activity performance information, such as daily sleeping hours, bedtime, number of steps walked, travel distance, contents of meals, caloric intake, and caloric consumption, records of the depth of sleep measured by the depth-of-sleep measuring unit 12, the cycle of the depth of sleep, as well as the results of learning of the depth of awakening sleep and the depth of nonawakening sleep.

More specifically, for example, the user information receiving unit 22 is implemented in the server 300 as a communication apparatus that receives information as described above transmitted from the mobile terminal 200 or as a program module that accepts information received by the communication apparatus. As will be described later, since a similar user is extracted from a plurality of users in the example illustrated in the drawing, the user information receiving unit 22 receives information as described above for the plurality of users.

A user information recording unit 23 records information received by the user information receiving unit 22 for each user. More specifically, the user information recording unit 23 is achieved by a memory or a storage of the server 300. Alternatively, the user information recording unit 23 may be achieved by an external storage that the server 300 can utilize.

A user characteristic extracting unit 24 extracts characteristics of each user from the information recorded in the user information recording unit 23. A similar user extracting unit 25 extracts users similar to one another in accordance with characteristics of the respective users extracted by the user characteristic extracting unit 24. For example, the user characteristic extracting unit 24 extracts characteristics in attribute information, activity performance information, and the like for all the users whose information has been recorded in the user information recording unit 23, and the similar user extracting unit 25 may cluster all the users in accordance with extracted characteristics. In this case, by previously classifying similar users into the same cluster, information on similar users can easily be transmitted when information on the similar users is requested from the user-side functions.

Alternatively, the user characteristic extracting unit 24 may extract characteristics of a user whose information has been received by the user information receiving unit 22 (who may be a user for which information on a similar user has been requested), and the similar user extracting unit 25 may extract a user having data indicating characteristics similar to characteristics of that user from the user information recording unit 23. In this case, a similar user can be extracted in conformity with information available for a target user, for example. For example, in a case where characteristics of the depth of sleep (more specifically, any of the first depth-of-sleep threshold value $D_e$, the second depth-of-sleep threshold value $D_h$, and the varying cycle of the depth of sleep, for example) have already been specified for the target user, the user characteristic extracting unit 24 can extract characteristics of the depth of sleep of each user from the information recorded in the user information recording unit 23, and the similar user extracting unit 25 can extract a user who is similar in the characteristics as a similar user. Accordingly, in a case where a part of characteristics of the depth of sleep (for example, the varying cycle of the depth of sleep) of some user has not been learned, for example, it can be complemented by characteristics already learned for another user who is similar in other characteristics of the depth of sleep.

The information transmitting unit 26 reads, from the user information recording unit 23, information on the similar user extracted by the similar user extracting unit 25, and transmits the information to the user-side functions. More specifically, the information transmitting unit 26 transmits information about a result of learning of the varying cycle of the depth of sleep, a depth-of-awakening-sleep region (the first depth-of-sleep threshold value $D_e$), a depth-of-nonawakening-sleep region (the second depth-of-sleep threshold value $D_h$), or the like of the similar user to the user-side functions. In the user-side functions provided with these pieces of information, the sleep environment controlling unit 17 will decide the temporal pattern of sleeping environment control on the basis of the varying cycle of the depth of sleep, the first depth-of-sleep threshold value $D_e$, the second depth-of-sleep threshold value $D_h$, or the like estimated for another user similar to the target user.

In this manner, in the present embodiment, even in a case where the depth-of-sleep cycle learning unit 14 has not collected sufficient time series data for estimating the varying cycle of the depth of sleep for the target user, processing in the environment control target setting unit 16 and the sleep environment controlling unit 17 can be executed in the user-side functions on the basis of data on the varying cycle of the depth of sleep estimated for a user similar to the target user. Moreover, as to the depth of awakening sleep and the depth of nonawakening sleep, even in a case where the depth-of-awakening-sleep estimating unit 20 and the depth-of-nonawakening-sleep estimating unit 21 have not collected sufficient data for learning, processing in the environment control target setting unit 16 and the sleep environment controlling unit 17 can be executed similarly on the basis of data on the depth of awakening sleep and the depth of nonawakening sleep estimated for a user similar to the target user.

Here, in a case of executing processing on the basis of data on the similar user provided by the information transmitting unit 26, it is expected that the accuracy will be degraded as compared with execution of processing on the basis of a value estimated on the basis of data on the target user by the depth-of-sleep cycle learning unit 14, the depth-of-awakening-sleep estimating unit 20, and the depth-of-nonawakening-sleep estimating unit 21. However, it is estimated that data on a similar user extracted on the basis of other available data is closer to data on the target user as the similarity between the users is higher.

In addition, as another additional component in the present embodiment, the sleep environment controlling unit 17 may decide the type of sleeping environment control or the temporal pattern of sleeping environment control in accordance with circumstances of the user. More specifically, for example, the sleep environment controlling unit 17 may change the method or intensity of changing (stimulating) the sleeping environment, the length of time or timing of giving stimuli in accordance with circumstances of the user, such as being on a trip or on a business trip. The circumstances of the user can be specified from, for example, user's positional information, schedule, contents of a message, or the like provided from a device in the system 10 such as the mobile terminal 200 or a device external to the system 10 capable of acquiring information, in addition to biological information or activity information, for example.

(4. Examples of User Interface)

Figure 9:
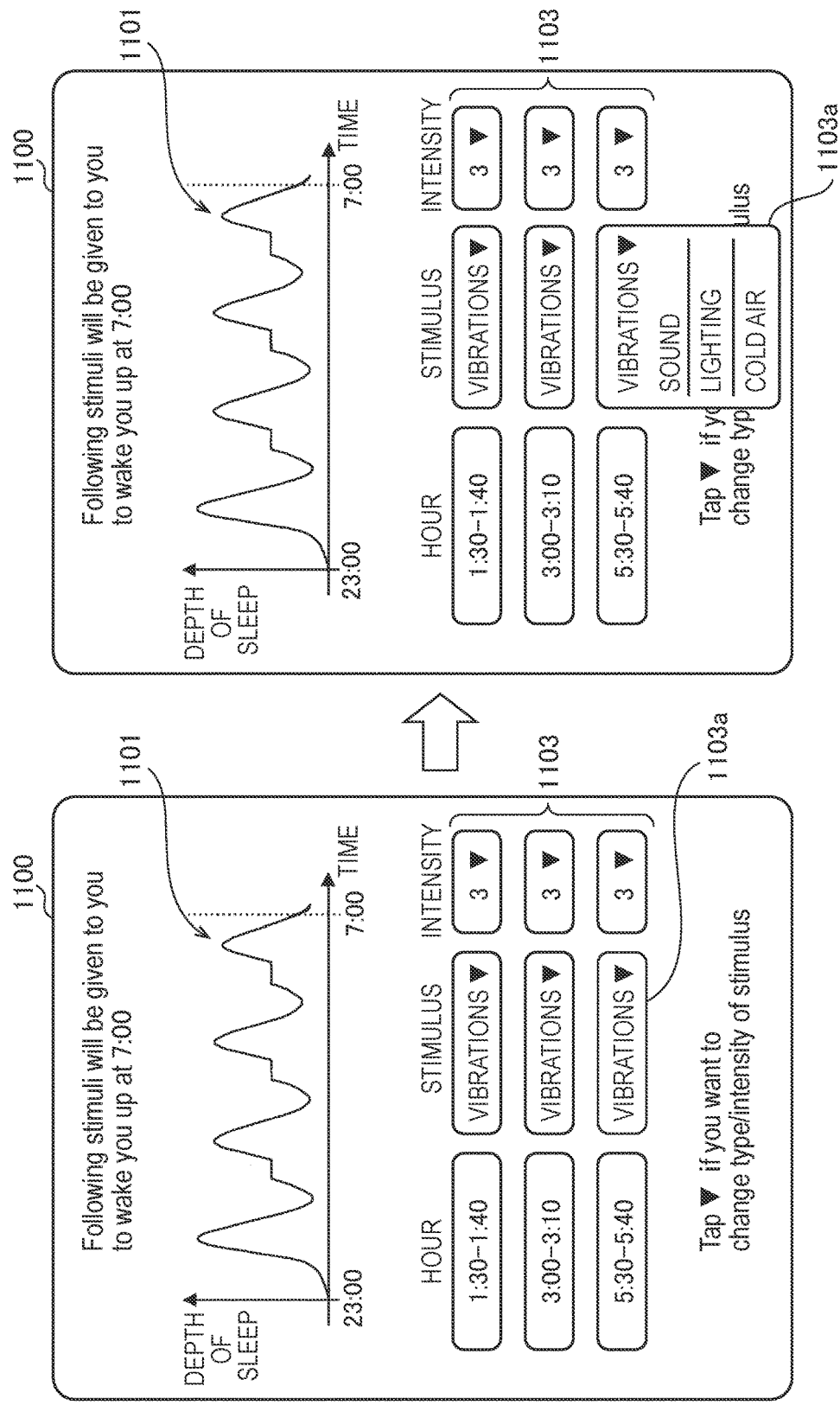
FIG. 9 is a view illustrating a first example of a user interface provided in an embodiment of the present disclosure.

FIG. 9 is a view illustrating a first example of a user interface provided in an embodiment of the present disclosure. In FIG. 9, a screen 1100 displayed on a display of the mobile terminal 200, for example, is illustrated. The screen 1100 includes a depth-of-sleep transition forecasting graph 1101 and a sleeping environment control schedule list 1103. In the graph 1101, a transition forecast of the depth of sleep before the user's rising time (a second time) having been forecast by the depth-of-sleep forecasting unit 15 assuming the user's bedtime (depth of sleep=0) as a first time is illustrated. Here, the transition forecast includes changes in transition of the depth of sleep caused by sleeping environment control currently scheduled (as displayed by the list 1103) in accordance with a target set by the environment control target setting unit 16.

A user referred to the screen 1100 can grasp what sleeping environment control is scheduled to be executed during sleep by the graph 1101 and the list 1103. Furthermore, in the example illustrated in the drawing, the list 1103 can be changed by a user operation, and a user can change contents of sleeping environment control. More specifically, the user is going to change the type of change (stimulus) in sleeping environment shown by an element 1103a in the list 1103. In the example illustrated in the drawing, the type of stimulus can be selected from among four types of vibrations, sound, lighting, and cold air. In addition, the intensity of the stimulus can also be set stepwise.

As described above, in a case where the contents of sleeping environment control are changed by changes in the list 1103, a forecast of the transition of the depth of sleep by the depth-of-sleep forecasting unit 15 is executed again, and the graph 1101 is updated. This allows the user to check how the transition of the depth of sleep will be changed by the change in the contents of sleeping environment control. At this time, in such a case where the forecast depth of sleep at the rising time falls out of the depth of awakening sleep, an alert may be output to prompt the user to change the contents of sleeping environment control again.

Figure 10:
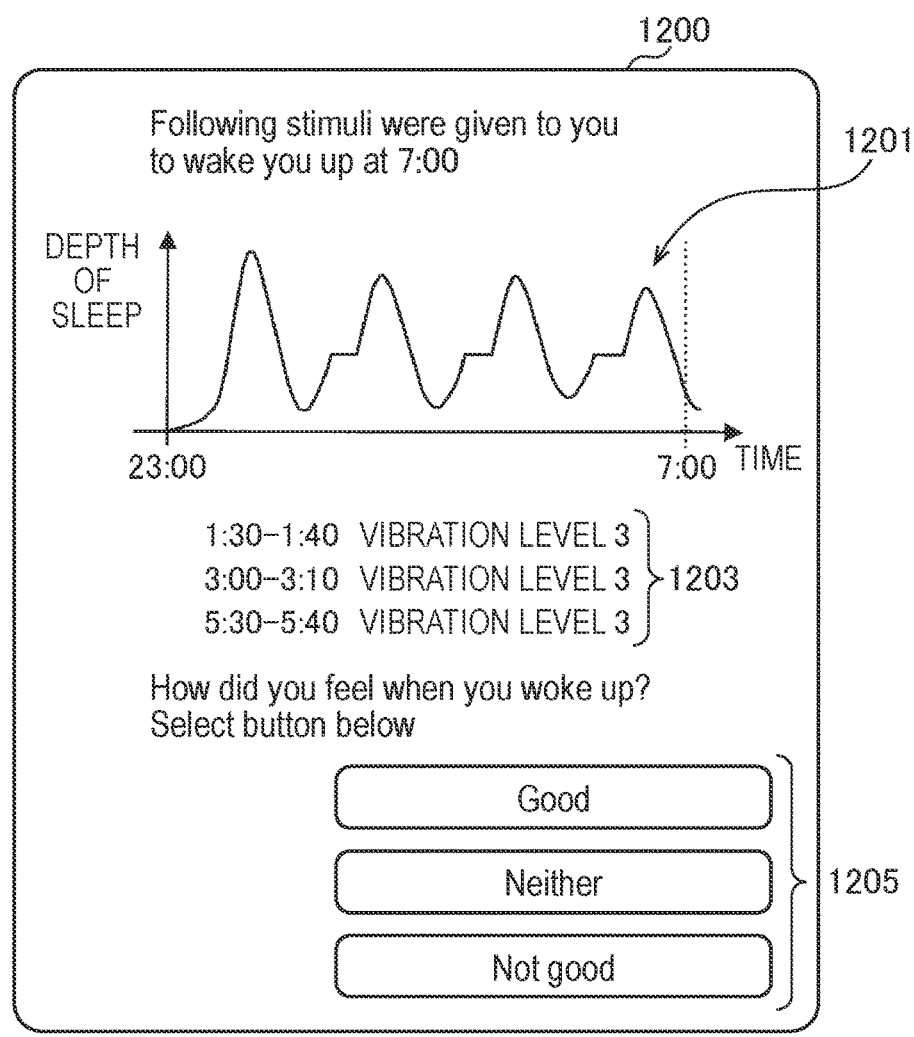
FIG. 10 is a view illustrating a second example of a user interface provided in an embodiment of the present disclosure.

FIG. 10 is a view illustrating a second example of a user interface provided in an embodiment of the present disclosure. In FIG. 10, a screen 1200 displayed on the display of the mobile terminal 200, for example, is illustrated. The screen 1200 includes a depth-of-sleep transition result graph 1201, a sleeping environment control result list 1203, and feedback input buttons 1205. In the graph 1201, a transition result of the depth of sleep from the user's bedtime to the rising time is shown. Moreover, sleeping environment controls executed from the user's bedtime to the rising time are displayed in the list 1203.

A user referred to the screen 1200 can grasp what sleeping environment controls were executed during sleep and how the depth of sleep transitioned consequently from the graph 1201 and the list 1203. Then, the user can input an impression at awakening by means of the input buttons 1205. In the example illustrated in the drawing, three types of input buttons 1205 of "good", "neither", and "not good" are prepared for an impression at awakening. As described above, a feedback input screen such as the screen 1200 is displayed by control by the feedback-input-screen display controlling unit 18 included in the system 10. In addition, feedback input by means of the input buttons 1205 or the like is received by the feedback receiving unit 19, and is used for estimating the range of the depth of awakening sleep by the depth-of-awakening-sleep estimating unit 20.

(5. Hardware Configuration)

Figure 11:
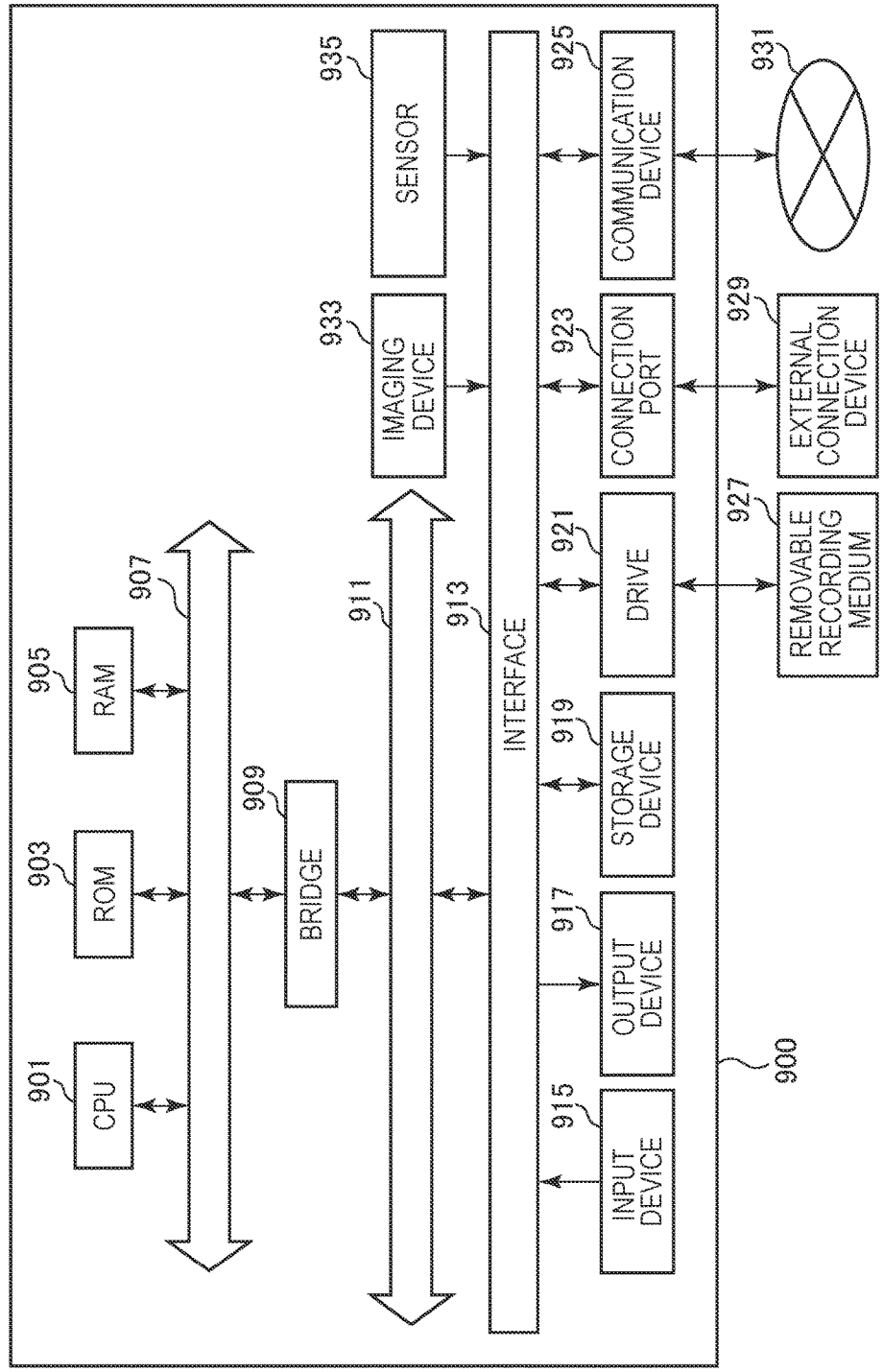
FIG. 11 is a block diagram illustrating a hardware configuration example of an information processing device according to an embodiment of the present disclosure.

Next, with reference to FIG. 11, a hardware configuration of an information processing apparatus according to an embodiment of the present disclosure is explained. FIG. 11 is a block diagram illustrating a hardware configuration example of an information processing apparatus according to the embodiment of the present disclosure. An illustrated information processing apparatus 900 may achieve each device to configure the system 10 in the above-mentioned embodiments, for example.

The information processing apparatus 900 includes a central processing unit (CPU) 901, read only memory (ROM) 903, and random access memory (RAM) 905. In addition, the information processing apparatus 900 may include a host bus 907, a bridge 909, an external bus 911, an interface 913, an input apparatus 915, an output apparatus 917, a storage apparatus 919, a drive 921, a connection port 923, and a communication apparatus 925. Moreover, the information processing apparatus 900 may include an imaging apparatus 933, and a sensor 935, as necessary. The information processing apparatus 900 may include a processing circuit such as a digital signal processor (DSP), an application-specific integrated circuit (ASIC), or a field-programmable gate array (FPGA), alternatively or in addition to the CPU 901.

The CPU 901 serves as an arithmetic processing apparatus and a control apparatus, and controls the overall operation or a part of the operation of the information processing apparatus 900 according to various programs recorded in the ROM 903, the RAM 905, the storage apparatus 919, or a removable recording medium 927. The ROM 903 stores programs, operation parameters, and the like used by the CPU 901. The RAM 905 transiently stores programs used when the CPU 901 is executed, and various parameters that change as appropriate when executing such programs. The CPU 901, the ROM 903, and the RAM 905 are connected with each other via the host bus 907 configured from an internal bus such as a CPU bus or the like. The host bus 907 is connected to the external bus 911 such as a Peripheral Component Interconnect/Interface (PCI) bus via the bridge 909.

The input apparatus 915 is a device operated by a user such as a mouse, a keyboard, a touch panel, a button, a switch, and a lever. The input apparatus 915 may be a remote control device that uses, for example, infrared radiation and another type of radiowave. Alternatively, the input apparatus 915 may be an external connection apparatus 929 such as a mobile phone that corresponds to an operation of the information processing apparatus 900. The input apparatus 915 includes an input control circuit that generates input signals on the basis of information which is input by a user to output the generated input signals to the CPU 901. A user inputs various types of data to the information processing apparatus 900 and instructs the information processing apparatus 900 to perform a processing operation by operating the input apparatus 915.

The output apparatus 917 includes an apparatus that can report acquired information to a user visually, audibly, or haptically. The output apparatus 917 may be, for example, a display device such as a liquid crystal display (LCD) or an organic electro-luminescence (EL) display, an audio output apparatus such as a speaker or a headphone, or a vibrator. The output apparatus 917 outputs a result obtained through a process performed by the information processing apparatus 900, in the form of video such as text and an image, sounds such as voice and audio sounds, or vibration.

The storage apparatus 919 is an apparatus for data storage that is an example of a storage unit of the information processing apparatus 900. The storage apparatus 919 includes, for example, a magnetic storage device such as a hard disk drive (HDD), a semiconductor storage device, an optical storage device, or a magneto-optical storage device. The storage apparatus 919 stores therein the programs and various data executed by the CPU 901, various data acquired from an outside, and the like.

The drive 921 is a reader/writer for the removable recording medium 927 such as a magnetic disk, an optical disc, a magneto-optical disk, and a semiconductor memory, and built in or externally attached to the information processing apparatus 900. The drive 921 reads out information recorded on the mounted removable recording medium 927, and outputs the information to the RAM 905. The drive 921 writes the record into the mounted removable recording medium 927.

The connection port 923 is a port used to connect devices to the information processing apparatus 900. The connection port 923 may include a Universal Serial Bus (USB) port, an IEEE1394 port, and a Small Computer System Interface (SCSI) port. The connection port 923 may further include an RS-232C port, an optical audio terminal, a High-Definition Multimedia Interface (HDMI) (registered trademark) port, and so on. The connection of the external connection device 929 to the connection port 923 makes it possible to exchange various data between the information processing apparatus 900 and the external connection device 929.

The communication apparatus 925 is a communication interface including, for example, a communication device for connection to a communication network 931. The communication apparatus 925 may be, for example, a communication card for a local area network (LAN), Bluetooth (registered trademark), Wi-Fi, or a wireless USB (WUSB). The communication apparatus 925 may also be, for example, a router for optical communication, a router for asymmetric digital subscriber line (ADSL), or a modem for various types of communication. For example, the communication apparatus 925 transmits and receives signals in the Internet or transits signals to and receives signals from another communication device by using a predetermined protocol such as TCP/IP. The communication network 931 to which the communication apparatus 925 connects is a network established through wired or wireless connection. The communication network 931 may include, for example, the Internet, a home LAN, infrared communication, radio communication, or satellite communication.

The imaging apparatus 933 is an apparatus that captures an image of a real space by using an image sensor such as a charge coupled device (CCD) and a complementary metal oxide semiconductor (CMOS), and various members such as a lens for controlling image formation of a subject image onto the image sensor, and generates the captured image. The imaging apparatus 933 may capture a still image or a moving image.

The sensor 935 is various sensors such as an acceleration sensor, an angular velocity sensor, a geomagnetic sensor, an illuminance sensor, a temperature sensor, a barometric sensor, and a sound sensor (microphone). The sensor 935 acquires information regarding a state of the information processing apparatus 900 such as a posture of a housing of the information processing apparatus 900, and information regarding an environment surrounding the information processing apparatus 900 such as luminous intensity and noise around the information processing apparatus 900. The sensor 935 may include a global positioning system (GPS) receiver that receives GPS signals to measure latitude, longitude, and altitude of the apparatus.

The example of the hardware configuration of the information processing apparatus 900 has been described. Each of the structural elements described above may be configured by using a general purpose member or may be configured by hardware specialized for the function of each of the structural elements. The configuration may be changed as necessary in accordance with the state of the art at the time of working of the present disclosure.

(6. Supplement)

The embodiments of the present disclosure may include, for example, the above-described information processing device (the wearable terminal 100*a*, the lighting device 100*b*, the mobile terminal 200, or the server 300), the above-described system, the information processing method executed by the information processing device or the system, a program for causing the information processing device to exhibit its function, and a non-transitory physical medium having the program stored therein.

The preferred embodiment(s) of the present disclosure has/have been described above with reference to the accompanying drawings, whilst the technical scope of the present disclosure is not limited to the above examples. A person skilled in the art may find various alterations and modifications within the scope of the technical idea recited in the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing device including:

a sleep environment controlling unit configured to, when exerting control of, on the basis of a result of forecast of a transition of a depth of sleep of a user at least in a period from a first time to a second time, a sleeping environment of the user such that the depth of sleep at the second time falls below a first depth-of-sleep threshold value estimated as an upper limit of a first depth-of-sleep region in which the user is likely to awake, decide a temporal pattern of the control in the period from the first time to the second time in accordance with a temporal pattern of the transition.

(2)

The information processing device according to (1), in which the temporal pattern of the transition includes a cyclical variation of the depth of sleep across a second depth-of-sleep threshold value estimated as a lower limit of a second depth-of-sleep region in which the user is unlikely to awake, and the temporal pattern of the control includes exerting control of the sleeping environment in a distributed manner among a plurality of times at which the depth of sleep is forecast to exceed the second depth-of-sleep threshold value.

(3)

The information processing device according to (2), in which the temporal pattern of the control includes equally distributing the control of the sleeping environment among the plurality of times.

(4)

The information processing device according to (2), in which the temporal pattern of the control includes distributing the control of the sleeping environment in a larger ratio to a time closer to the first time among the plurality of times.

(5)

The information processing device according to any one of (2) to (4), in which the control of the sleeping environment produces a delay in the transition of the depth of sleep.

(6)

The information processing device according to any one of (2) to (5), in which the second depth-of-sleep threshold value is estimated on the basis of whether the user awakes when the control of the sleeping environment is exerted for the user.

(7)

The information processing device according to any one of (2) to (5), in which the second depth-of-sleep threshold value is a value estimated for another user similar to the user.

(8)

The information processing device according to (1), in which the temporal pattern of the transition includes a cyclical variation of the depth of sleep, the temporal pattern of the control includes controlling the sleeping environment continuously from the first time to the second time, and the control of the sleeping environment produces a change in varying cycle of the depth of sleep.

(9)

The information processing device according to any one of (1) to (8), in which the first depth-of-sleep threshold value is estimated on the basis of feedback from the user acquired after the user awakes.

(10)

The information processing device according to any one of (1) to (8), in which the first depth-of-sleep threshold value is a value estimated for another user similar to the user.

(11)

The information processing device according to any one of (1) to (10), in which the temporal pattern of the transition includes a cyclical variation of the depth of sleep, and the sleep environment controlling unit decides the temporal pattern of the control in accordance with a varying cycle of the depth of sleep estimated on the basis of transition performance of the depth of sleep.

(12)

The information processing device according to any one of (1) to (10), in which the temporal pattern of the transition includes a cyclical variation of the depth of sleep, and the sleep environment controlling unit decides the temporal pattern of the control in accordance with a varying cycle of the depth of sleep estimated for another user similar to the user.

(13)

The information processing device according to any one of (7), (10), and (12), in which the other user similar to the user is extracted on the basis of similarity of characteristics in attribute, activity performance, or depth of sleep between the user and the other user.

(14)

The information processing device according to (13), in which the characteristic of the depth of sleep includes any of the first depth-of-sleep threshold value, a second depth-of-sleep threshold value estimated as a lower limit of a second depth-of-sleep region in which the user is unlikely to awake, and a varying cycle of the depth of sleep.

(15)

The information processing device according to any one of (1) to (14), in which the sleep environment controlling unit decides a type of the control or the temporal pattern of the control in accordance with a circumstance of the user.

(16)

The information processing device according to any one of (1) to (15), in which the sleep environment controlling unit decides a type of the control in accordance with the temporal pattern of the transition.

(17)

An information processing method including:

when exerting control of, on the basis of a result of forecast of a transition of a depth of sleep of a user at least in a period from a first time to a second time, a sleeping environment of the user such that the depth of sleep at the second time falls below a first depth-of-sleep threshold value estimated as an upper limit of a first depth-of-sleep region in which the user is likely to awake, causing a processor to decide a temporal pattern of the control in the period from the first time to the second time in accordance with a temporal pattern of the transition.

(18)

A program for causing a computer to achieve a function of, when exerting control of, on the basis of a result of forecast of a transition of a depth of sleep of a user at least in a period from a first time to a second time, a sleeping environment of the user such that the depth of sleep at the second time falls below a first depth-of-sleep threshold value estimated as an upper limit of a first depth-of-sleep region in which the user is likely to awake, deciding a temporal pattern of the control in the period from the first time to the second time in accordance with a temporal pattern of the transition.

REFERENCE SIGNS LIST 10 system
11 rising time setting unit
12 depth-of-sleep measuring unit
13 sleeping environment measuring unit
14 depth-of-sleep cycle learning unit
15 depth-of-sleep forecasting unit
16 environment control target setting unit
17 sleep environment controlling unit
18 feedback-input-screen display controlling unit
19 feedback receiving unit
20 depth-of-awakening-sleep estimating unit
21 depth-of-nonawakening-sleep estimating unit
22 user information receiving unit
23 user information recording unit
24 user characteristic extracting unit
25 similar user extracting unit
26 information transmitting unit
100a wearable terminal
100b lighting device
200 mobile terminal
300 server

The invention claimed is:

1. An information processing device, comprising:
a sleep environment controlling unit configured to, when exerting control of, based on a result of forecast of a transition of a depth of sleep of a user at least in a period from a first time to a second time, a sleeping environment of the user such that the depth of sleep at the second time falls below a first depth-of-sleep threshold value estimated as an upper limit of a first depth-of-sleep region in which the user is likely to awake, decide a temporal pattern of the control in the period from the first time to the second time in accordance with a temporal pattern of the transition.

2. The information processing device according to claim 1, wherein
the temporal pattern of the transition includes a cyclical variation of the depth of sleep across a second depth-of-sleep threshold value estimated as a lower limit of a second depth-of-sleep region in which the user is unlikely to awake, and
the temporal pattern of the control includes exerting control of the sleeping environment in a distributed manner among a plurality of times at which the depth of sleep is forecast to exceed the second depth-of-sleep threshold value.

3. The information processing device according to claim 2, wherein
the temporal pattern of the control includes an equal distribution of the control of the sleeping environment among the plurality of times.

4. The information processing device according to claim 2, wherein
the temporal pattern of the control includes distribution of the control of the sleeping environment in a larger ratio to a time closer to the first time among the plurality of times.

5. The information processing device according to claim 2, wherein
the control of the sleeping environment produces a delay in the transition of the depth of sleep.

6. The information processing device according to claim 2, wherein
the second depth-of-sleep threshold value is estimated based on whether the user awakes when the control of the sleeping environment is exerted for the user.

7. The information processing device according to claim 2, wherein
the second depth-of-sleep threshold value is a value estimated for another user similar to the user.

8. The information processing device according to claim 1, wherein:
the temporal pattern of the transition includes a cyclical variation of the depth of sleep,
the temporal pattern of the control includes control of the sleeping environment continuously from the first time to the second time, and
the control of the sleeping environment produces a change in varying cycle of the depth of sleep.

9. The information processing device according to claim 1, wherein
the first depth-of-sleep threshold value is estimated based on feedback from the user acquired after the user awakes.

10. The information processing device according to claim 1, wherein
the first depth-of-sleep threshold value is a value estimated for another user similar to the user.

11. The information processing device according to claim 1, wherein
the temporal pattern of the transition includes a cyclical variation of the depth of sleep, and
the sleep environment controlling unit decides the temporal pattern of the control in accordance with a varying cycle of the depth of sleep estimated based on transition performance of the depth of sleep.

12. The information processing device according to claim 1, wherein
the temporal pattern of the transition includes a cyclical variation of the depth of sleep, and
the sleep environment controlling unit decides the temporal pattern of the control in accordance with a varying cycle of the depth of sleep estimated for another user similar to the user.

13. The information processing device according to claim 12, wherein
the other user similar to the user is extracted based on similarity of characteristics in at least one of attribute, activity performance, or depth of sleep between the user and the other user.

14. The information processing device according to claim 13, wherein
the characteristic of the depth of sleep includes at least one of the first depth-of-sleep threshold value, a second depth-of-sleep threshold value estimated as a lower limit of a second depth-of-sleep region in which the user is unlikely to awake, and a varying cycle of the depth of sleep.

15. The information processing device according to claim 1, wherein
the sleep environment controlling unit further decides a type of the control or the temporal pattern of the control in accordance with a circumstance of the user.

16. The information processing device according to claim 1, wherein
the sleep environment controlling unit further decides a type of the control in accordance with the temporal pattern of the transition.

17. An information processing method, comprising:
when exerting control of, based on a result of forecast of a transition of a depth of sleep of a user at least in a period from a first time to a second time, a sleeping environment of the user such that the depth of sleep at the second time falls below a first depth-of-sleep threshold value estimated as an upper limit of a first depth-of-sleep region in which the user is likely to awake, causing a processor to decide a temporal pattern of the control in the period from the first time to the second time in accordance with a temporal pattern of the transition.

18. A non-transitory computer-readable medium having stored thereon computer-executable instructions that, when executed by a computer, cause the computer to perform operations, the operations comprising: when exerting control of, based on a result of forecast of a transition of a depth of sleep of a user at least in a period from a first time to a second time, a sleeping environment of the user such that the depth of sleep at the second time falls below a first depth-of-sleep threshold value estimated as an upper limit of a first depth-of-sleep region in which the user is likely to awake, deciding a temporal pattern of the control in the period from the first time to the second time in accordance with a temporal pattern of the transition.

* * * * *